United States Patent [19]

Sie

[11] Patent Number: 5,292,983

[45] Date of Patent: Mar. 8, 1994

[54] PROCESS FOR THE PRODUCTION OF ISOPARAFFINS

[75] Inventor: Swan T. Sie, Amsterdam, Netherlands

[73] Assignee: Shell Oil Company, Houston, Tex.

[21] Appl. No.: 880,107

[22] Filed: May 6, 1992

[30] Foreign Application Priority Data

May 7, 1991 [GB] United Kingdom ................ 9109747

[51] Int. Cl.$^5$ ............................ C07C 4/06; C07C 5/27
[52] U.S. Cl. ..................... 585/733; 585/310; 585/750; 585/752; 585/820
[58] Field of Search ............. 585/733, 750, 310, 946; 208/950

[56] References Cited

U.S. PATENT DOCUMENTS

| | | | |
|---|---|---|---|
| 3,268,439 | 8/1966 | Tupman et al. | 585/749 |
| 3,702,874 | 11/1972 | Estes et al. | 208/112 |
| 3,711,399 | 1/1973 | Estes et al. | 208/112 |
| 4,044,063 | 8/1977 | Ireland et al. | 260/676 |
| 4,045,505 | 8/1977 | Ireland et al. | 260/673 |
| 4,059,648 | 11/1977 | Derr et al. | 260/676 |
| 4,080,397 | 3/1978 | Derr et al. | 260/676 |
| 4,111,792 | 9/1978 | Caesar et al. | 208/79 |
| 4,126,644 | 11/1978 | Caesar et al. | 260/676 |
| 4,385,193 | 5/1983 | Bijwaard et al. | 585/310 |
| 4,423,265 | 12/1983 | Chu et al. | 585/322 |
| 4,471,145 | 9/1984 | Chu et al. | 585/322 |
| 4,500,417 | 2/1985 | Chen et al. | 208/111 |
| 4,522,939 | 6/1985 | Minderhoud et al. | 502/242 |
| 4,523,047 | 6/1985 | Chester et al. | 585/322 |
| 4,594,468 | 6/1986 | Minderhoud et al. | 585/310 |
| 4,605,680 | 8/1986 | Beuther et al. | 518/715 |
| 4,751,345 | 6/1988 | Mauldin | 585/733 |
| 4,762,959 | 8/1988 | Mauldin et al. | 581/640 |
| 4,832,819 | 5/1989 | Hamner | 585/748 |
| 4,943,672 | 7/1990 | Hamner et al. | 585/737 |

FOREIGN PATENT DOCUMENTS 1380004 3/1971 United Kingdom .

*Primary Examiner*—Anthony McFarlane

[57] ABSTRACT

A process for the production of isoparaffins having 4 to 7 carbon atoms per molecule from synthesis gas comprising the following steps:
  a) Synthesis of a heavy paraffins-containing hydrocarbon mixture over a Fischer-Tropsch catalyst;
  b) Conversion of at least part of the heavy paraffins-containing hydrocarbon mixture over a bi-functional isomerization/hydrocracking catalyst under isomerization/hydrocracking conditions;
  c) Separation of normal paraffins from at least part of the isoparaffins-containing product of step (b);
  d) Recycling at least part of the normal paraffins to step (b) and withdrawing $C_4$–$C_7$ isoparaffins as a product from the process.

18 Claims, 3 Drawing Sheets

PROCESS FOR THE PRODUCTION OF ISOPARAFFINS

BACKGROUND OF THE INVENTION

1. Field of the Invention

The present invention relates to a process for the preparation of isoparaffins having 4 to 7 carbon atoms per molecule from synthesis gas including the following steps:
- a) synthesizing a heavy paraffins-containing hydrocarbon mixture over a Fischer-Tropsch catalyst;
- b) converting at least part of the heavy paraffins-containing hydrocarbon mixture over a bi-functional isomerization/hydrocracking catalyst under isomerization/hydrocracking conditions;
- c) separating the normal paraffins from at least part of the isoparaffins-containing product of step (b); and
- d) recycling at least part of the normal paraffins to step (b) and withdrawing the $C_4$-$C_7$ isoparaffins as a product.

2. Description of the Prior Art

In certain instances, it is desirable to produce a specific type of hydrocarbon because of its benefit in preparing a particular product. A number of different reactions for producing hydrocarbons have been practiced over the years. Fischer-tropsch synthesis, the contacting of a mixture of carbon monoxide and hydrogen with a suitable catalyst at an elevated temperature and pressure, is a well-known process for the production of various types of hydrocarbons. Only a small amount of iso-paraffins, a specific type of hydrocarbon which are of particular importance in preparing such products as gasolines and fuels, are produced utilizing the Fischer-Tropsch synthesis.

It has now been found that iso-paraffins may be produced in an efficient manner utilizing the process of the present invention.

SUMMARY OF THE INVENTION

A process for the production of isoparaffins having 4 to 7 carbon atoms per molecule from synthesis gas comprising the following steps:
- a) synthesizing a heavy paraffins-containing hydrocarbon mixture over a Fischer-Tropsch catalyst;
- b) converting at least part of the heavy paraffins-containing hydrocarbon mixture over a bi-functional isomerization/hydrocracking catalyst under isomerization/hydrocracking conditions;
- c) separating normal paraffins from at least part of the isoparaffins-containing product of step (b); and
- d) recycling at least part of the normal paraffins to step (b) and withdrawing $C_4$-$C_7$ isoparaffins as a product from the process.

DESCRIPTION OF THE PREFERRED EMBODIMENTS

Figure 1:
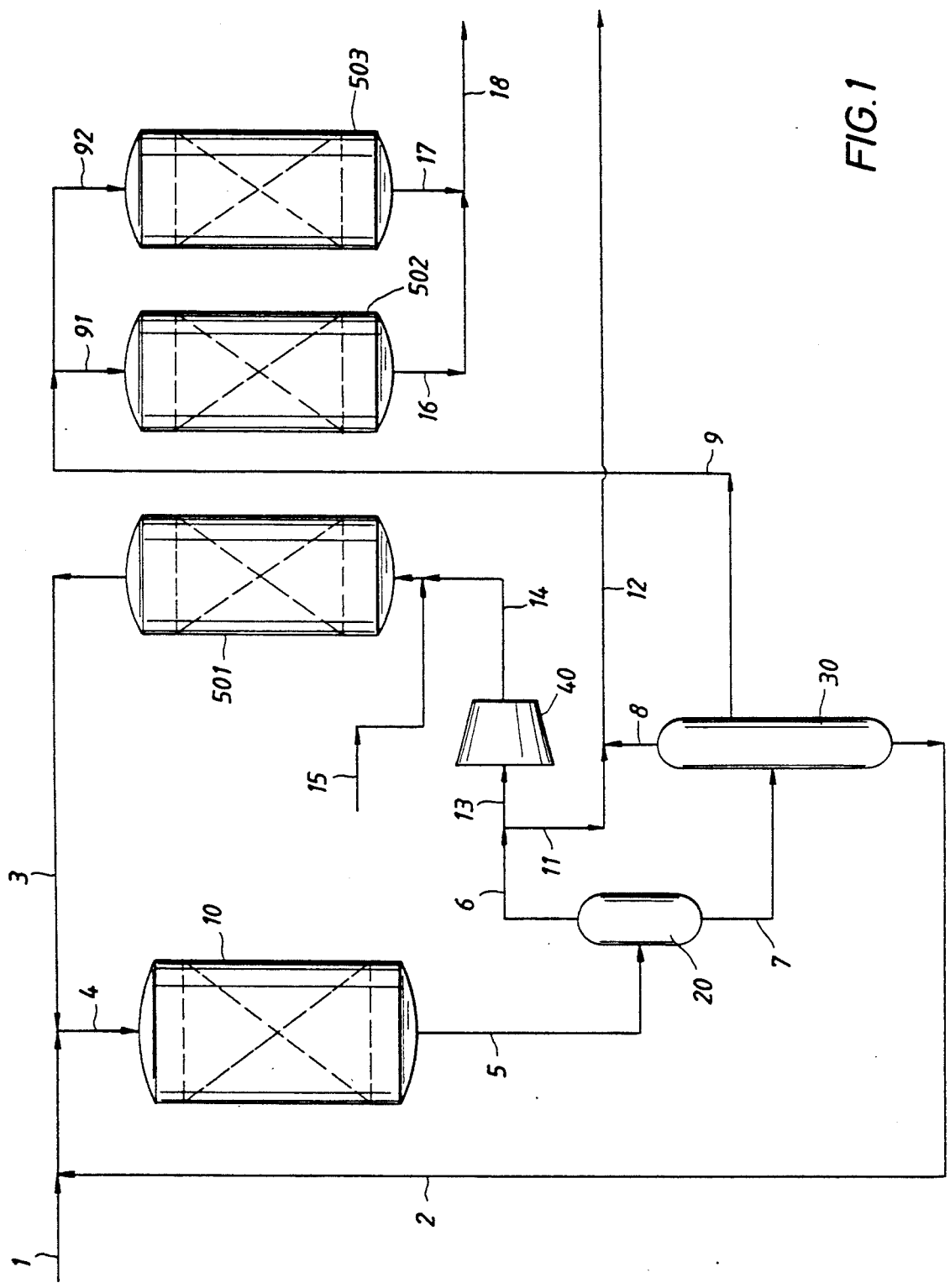
FIG. 1 is a schematic view showing the production of gasoline-range isoparaffins utilizing the present process.

In the process of the instant invention, isoparaffins having 4 to 7 carbons per molecule are prepared from synthesis gas by:
- a) synthesizing a heavy paraffins-containing hydrocarbon mixture over a Fischer-Tropsch catalyst;
- b) converting at least part of the heavy paraffins-containing hydrocarbon mixture over a bi-functional isomerization/hydrocracking catalyst under isomerization/hydrocracking conditions;
- c) separating the normal paraffins from at least part of the isoparaffins-containing product of step (b); and
- d) recycling at least part of the normal paraffins to step (b) and withdrawing the $C_4$-$C_7$ isoparaffins as a product from the process.

In the first step of the process of the present invention, a heavy paraffins-containing hydrocarbon mixture is synthesized using a Fischer-Tropsch catalyst containing one or more metals of the iron group together with one or more promoters and a carrier material. The preferred Fischer-Tropsch catalyst is a cobalt catalyst which contains cobalt, a silica carrier and at least one other metal chosen from the group consisting of zirconium, titanium, rhenium, ruthenium and chromium. The preferred metal is zirconium.

The catalyst utilized in the step (a) of the process of the present invention is preferably prepared by kneading, impregnation, or both kneading and impregnation and preferably satisfies the relation:

$$(3+4R) > L/S > (0.3+0.4R),$$

wherein
- L = the total quantity of cobalt present on the catalyst, expressed as mg Co/ml catalyst,
- S = the surface area of the catalyst, expressed as $m^2$/ml catalyst, and
- R = the weight ratio of the quantity of cobalt deposited on the catalyst by kneading to the total quantity of cobalt present on the catalyst.

The cobalt catalyst used in step (a) of the process of the present invention can be prepared according to any of the conventional methods for preparing Fischer-Tropsch catalysts.

The cobalt catalyst utilized preferably contains from about 3 pbw to about 60 pbw of cobalt, even more preferably from about 15 pbw to about 50 pbw of cobalt, per 100 pbw of carrier. The quantity of other metal present in the catalyst is from about 0.1 pbw to about 100 pbw per 100 pbw of carrier. The preferred amount of other metal present depends upon the manner in which this metal is deposited. When cobalt is deposited on the carrier first, followed by the addition of the other metal, preference is given to a catalyst containing from about 0.1 pbw to about 5 pbw other metal per 100 pbw carrier. When the other metal is deposited on the carrier first, followed by the addition of cobalt, the catalyst preferably contains from about 5 pbw to about 40 pbw of the other metal per 100 pbw of carrier. Before being used, the catalyst should be reduced by contacting the catalyst with a hydrogen-containing gas at a temperature from about 200° C. to about 350° C.

Step (a) of the present process is carried out at a temperature from about 125° C. to about 350° C., preferably from about 175° C. to about 275° C., and a pressure of from about 5 bar to about 100 bar, preferably from about 10 bar to about 75 bar.

The $H_2$:CO mixtures to be used can be obtained by steam reforming, partial oxidation, or a combination of these processes starting with either a heavy carbonaceous material such as coal, or light hydrocarbons such as natural gas. The $H_2$:CO consumption ratio of the preferred cobalt catalyst is about 2. In those cases where the highest possible CO conversion is desired, it is preferred to use $H_2$:CO mixtures having a H2:CO molar ratio which is higher than about 2.

Following the completion of step (a), at least part of the heavy paraffins-containing hydrocarbon mixture produced in step (a) is hydrocracked and isomerized in step (b) of the process using a catalyst which preferably contains a catalytically active metal component deposited on any acid carrier having cracking and isomerization activity. A zeolitic carrier having a pore diameter in the range from about 0.5 microns to about 1.0 microns and a silica:alumina ratio in the range from about 5 to about 200 is preferably used. The zeolite should have an alkali-metal content of less than about 1% by weight, preferably of less than about 0.1% by weight. In order to make the zeolites suitable for use as carrier material, it is preferred to replace at least part of the alkali-metal ions present therein by other cations, in particular by hydrogen ions, ammonium ions, ions of the rare-earth metals, or combinations thereof. Suitable zeolites include, but are not limited to, zeolite Y, mordenite, zeolite $\beta$, ZSM-20 and mixtures thereof.

The zeolite-based hydrocracking catalyst preferably contains one or more metals selected from Groups VIB, VIIB, VIII of the Periodic Table of Elements or mixtures thereof, as catalytically active metal components. Catalysts with a noble metal as the catalytically active metal component generally contain from about 0.05 parts by weight to about 5 parts by weight, preferably from about 0.1 parts by weight to about 2 parts by weight, of metal per 100 parts by weight of carrier. Catalysts with a non-noble metal or a combination of non-noble metals as the catalytically active metal component generally contain from about 0.1 by weight to about 35 parts by weight of metal or combination of metals, per 100 parts by weight of carrier. The catalysts may also contain a combination of from about 0.5 parts by weight to about 20 parts by weight, preferably from about 1 part by weight to about 10 parts by weight, of a non-noble metal of Group VIII and from about 1 part by weight to about 30 parts by weight, preferably from about 2 parts by weight to about 20 parts by weight, of a metal of Group VIB, VIIB, or mixtures thereof, per 100 parts by weight of carrier. Particularly suitable metal combinations are combinations of nickel and/or cobalt with tungsten and/or molybdenum and/or rhenium.

If the hydrocracking catalyst utilized contains one or more non-noble metals as the catalytically active metal component, they are preferably used in their sulfide form. The conversion of the hydrocracking catalyst to its sulfide form can be carried out by contacting the catalyst at a temperature below about 500° C. with a mixture of hydrogen and hydrogen sulfide in a volume ratio of from about 5:1 to about 15:1 or by adding sulfur compounds to the feed, under reaction conditions, in a quantity from about 10 ppmw to about 5% by weight, preferably in a quantity from about 100 ppmw to about 2.5% by weight.

The metals can be applied in any conventional manner including, but not limited to, impregnation, percolation or ion exchange. After the catalytically active metal components have been applied to the carrier, the catalyst is usually dried and then calcined.

The hydrocracking/isomerization step (b) of the present invention is carried out at a temperature from about 250° C. to about 450° C., preferably from about 250° C. to about 350° C. The pressure utilized ranges from about 5 bar to about 50 bar, preferably from about 7 bar to about 15 bar. The hourly space velocity ranges from about 0.2 kg to about 20 kg of hydrocarbon feed per kg of catalyst per hour and the hydrogen/hydrocarbon feed molar ratio ranges from about 1 to about 50.

At least part of the effluent of the isomerization/hydrocracking step (b) is passed to an additional separation step (c) in which a hydrogen-containing gas and a hydrocarbon effluent are separated from each other. This separation step can be accomplished by flash distillation. The flash distillation is carried out at a temperature of from about $-20°$ C. to about 100° C., and a pressure of from about 1 bar to about 50 bar.

Preferably, at least part of the effluent of the isomerization/hydrocracking step (b) of the process of the present invention is separated by fractional distillation to obtain a $C_7-$ fraction and a $C_8+$ fraction. At least part of the $C_8+$ fraction is preferably recycled to step (b). At least part of the $C_7-$ fraction is preferably passed to a separatory molecular sieve capable of adsorbing normal hydrocarbons. The branched hydrocarbons found in the C7-fraction are not retained in any substantial amount by the molecular sieve and are separated off as a product stream. This selectivity is dependent to a large extent on the pore diameters of the molecular sieve. The diameters of the pores of the molecular seives are preferably in the range from about 0.3 nanometers to about 0.8 nanometers, and even more preferably from about 0.4 nanometers to about 0.6 nanometers. Suitably, the separation step comprises a separatory molecular sieve having a pore size which is sufficient to permit entry of normal hydrocarbons containing from about 4 to about 7 carbon atoms, but prohibits entry of mono-methyl branched, and dimethyl branched hydrocarbons.

Suitably, synthetic or natural zeolites, erionite and offretite are used as molecular sieves, with zeolite 5A being preferred. As noted above, each of these preferably have a pore diameter in the range from about 0.3 nanometers to about 0.8 nanometers, and even more preferably from about 0.4 nanometers to about 0.6 nanometers. The particles which comprise molecular sieve material may also comprise a binder material such as alumina, silica or silica-alumina, in order to improve the crushing strength of the particles. The particles may also be mixed with particles which do not contain molecular sieve material.

The adsorption using the separatory molecular seive in step (c) is carried out at a temperature in the range from about 50° C. to about 400° C., preferably from about 100° C. to about 300° C. and at a pressure in the range from about 3 bar to about 30 bar, preferably from about 5 bar to about 25 bar.

The hydrocarbons which are adsorbed on the separatory molecular sieve in step (c), can be desorbed therefrom by contacting the sieve with a liquid solvent or with a gas. Preferably, the adsorbed normal hydrocarbons are desorbed by passing a hydrogen-containing gas over the molecular sieve. At least part of the hydrogenand normal hydrocarbons-containing effluent of step (c) is recycled for use in step (b).

Hydrocarbons which are adsorbed on the separatory molecular sieve, can be periodically desorbed therefrom by interrupting the stream of hydrocarbon effluent and passing a hydrogen-containing gas over the separatory molecular sieve. After desorption of a substantial amount of the adsorbed hydrocarbons, the stream of hydrogen-containing gas is interrupted and the stream of hydrocarbon effluent from the isomerization step is contacted again with the sieve. It is possible to carry out the process such that a continuous stream containing normal hydrocarbons is obtained, e.g. by using several vessels. The hydrogen-containing gas which can be used for desorbing the adsorbed hydrocarbons, need not be completely pure and may contain a certain amount of other components, suitably up to about 40 mol %, preferably not more than about 20 mol % of other compounds such as hydrocarbons, e.g. reformer off-gas, provided that these compounds are substantially inert with respect to the feed and the separatory molecular sieve applied. The hydrogen-containing gas is passed over the molecular sieve at a temperature from about 200° C. to about 450° C. and a pressure of from about 1 bar to about 25 bar.

DETAILED DESCRIPTION OF THE DRAWINGS

Figure 2:
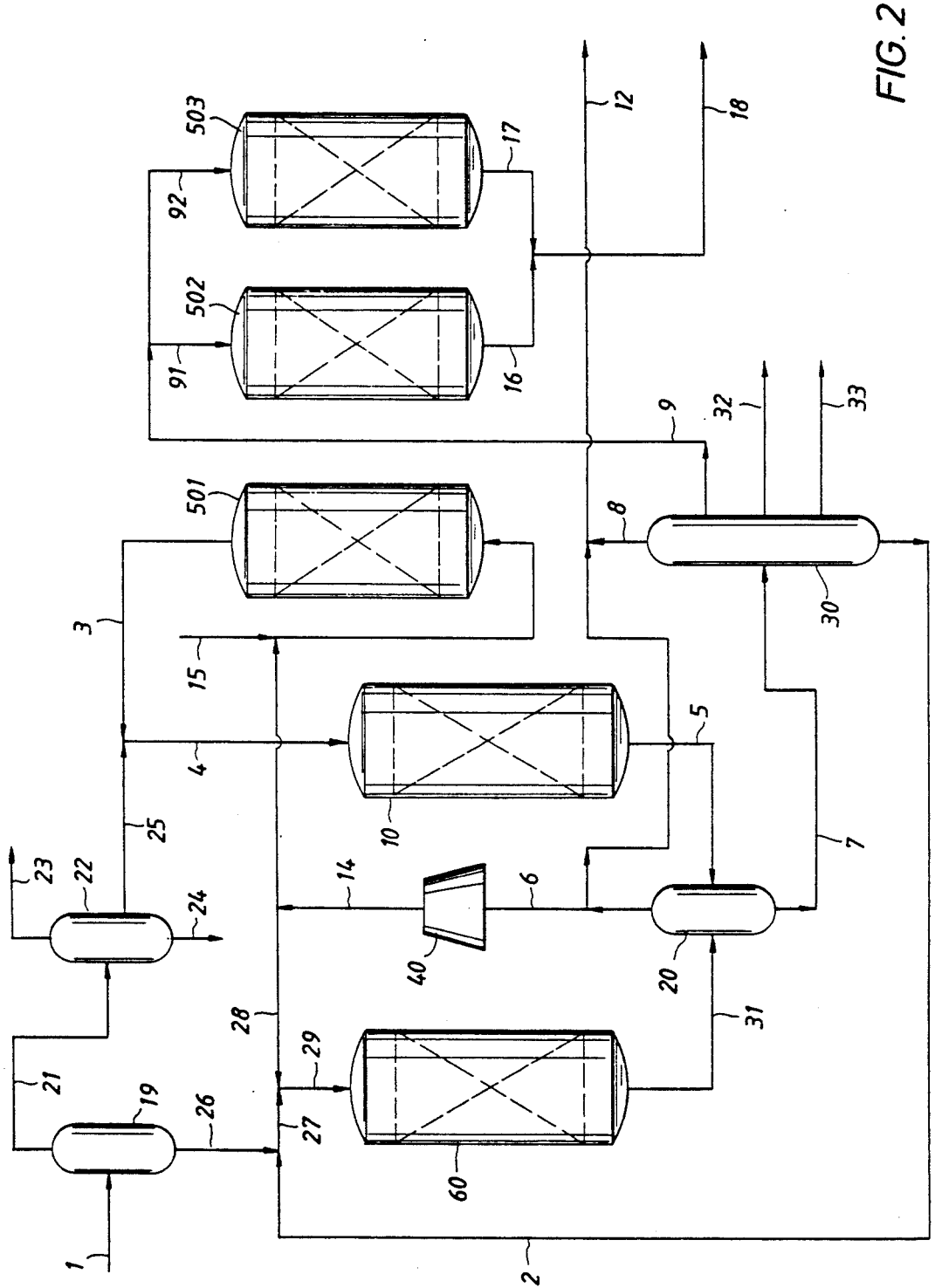
FIG. 2 is a schematic view showing the production of a $C_4$-$C_7$ isoparaffins-containing gasoline blending component, a $C_3$ and $C_4$ olefins-containing chemical feedstock, a kerosine fraction and a gas oil fraction utilizing the present process.
Figure 3:
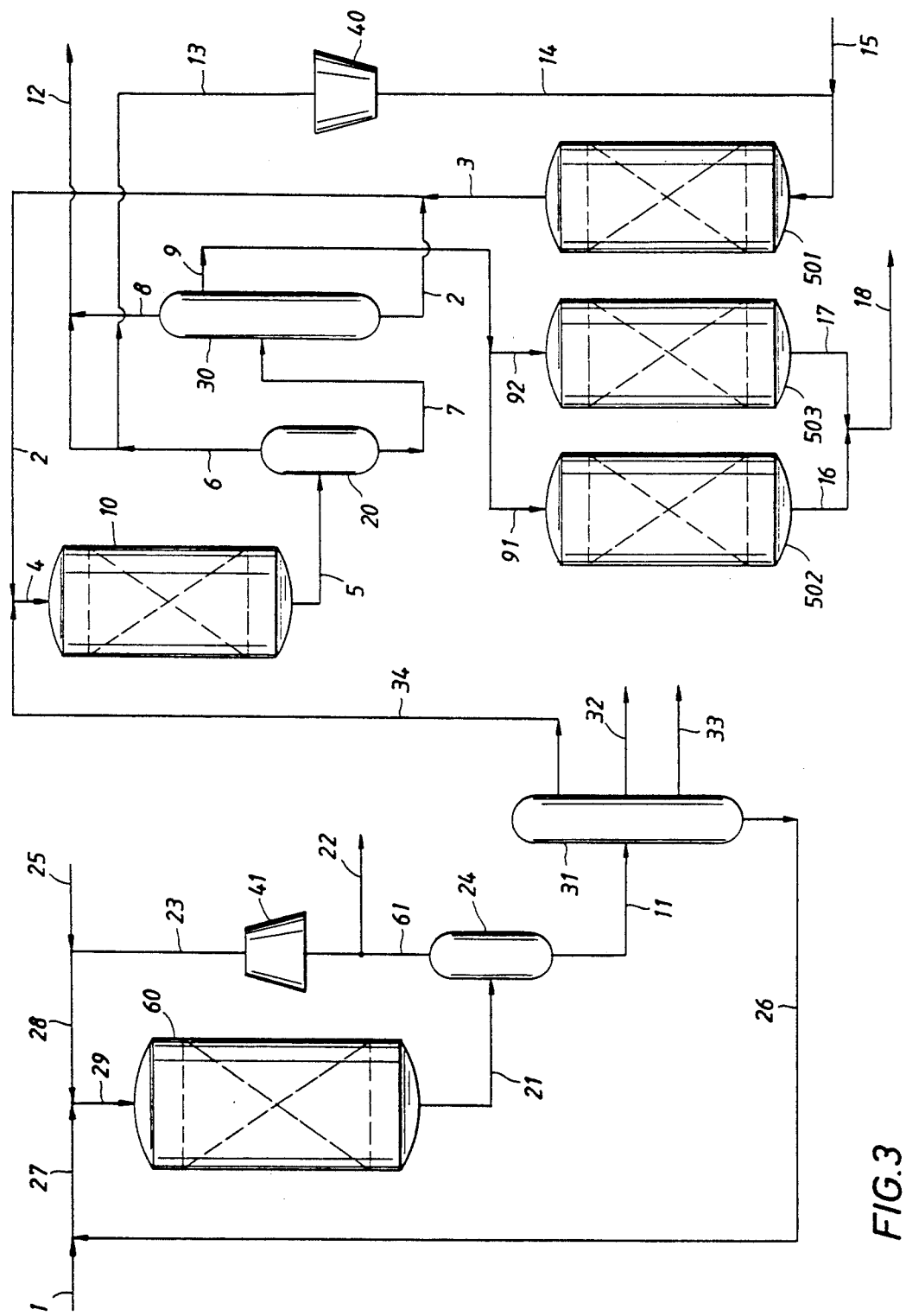
FIG. 3 is a schematic view showing the production of high octane $C_4$-$C_7$ isoparaffin gasoline components, high cetane gas oil and low smoke point kerosine utilizing the present process.

The process of the present invention can be carried out in a number of ways as depicted by FIGS. 1-3. These figures demonstrate various process schemes, but are in no way meant to restrict the invention. The processes depicted in the figures are carried out with the help of an isomerization/hydrocracking reactor 10, a product separator 20, a fractionator 30, a recycle gas compressor 40 and three iso/normal paraffins separators 501, 502 and 503.

In the process schematically shown in FIG. 1, gasoline-range isoparaffins are produced by converting the effluent from a Fischer-Tropsch hydrocarbon synthesis step (not shown). The Fischer-Tropsch effluent is introduced into the process via line 1. It is combined with a $C_8+$ recycle stream obtained via line 2 from the fractionator 30, and with a normal paraffins and hydrogen-containing recycle stream obtained via line 3 from the separator 501. Streams 1, 2 and 3 are combined and introduced via line 4 into the isomerization/ hydrocracking reactor 10 wherein higher boiling normal paraffins are at least in part hydrocracked and lower boiling normal paraffins are at least in part isomerized in the presence of hydrogen.

The effluent from the reactor 10 is passed via line 5 to the product separator 20 where it is separated into a hydrogen-rich gaseous stream which is withdrawn via line 6, and a hydrocarbons-containing liquid stream which is passed through line 7 to the fractionator 30 where it is separated into a light hydrocarbons (predominantly $C_3-$ stream which is withdrawn from the fractionator 30 via line 8, a $C_4-C_7$ iso/normal paraffins-containing stream which is transferred via-line 9, line 91 and line 92 to the iso/normal paraffins separators 502 and 503, and a $C_8+$ hydrocarbons-containing recycle stream which is recycled to the reactor 10 via lines 2 and 1. The hydrogen-containing stream which passes through line 6 is divided into two parts. One part is passed through line 11 to be combined with the light hydrocarbons-containing gaseous stream of line 8 and is withdrawn from the system via line 12.

The remaining part of the stream from line 6 is passed via line 13 to the recycle gas compressor 40 and line 14 to the iso/normal paraffins separator 501. Make-up hydrogen is supplied to the line 14 via line 15.

In the iso/normal paraffins separators 501, 502 and 503 the iso- and normal $C_4-C_7$ paraffins-containing mixture is separated into a $C_5-C_7$ isoparaffins- plus i- and n-$C_4$ paraffins-containing stream and a $C_5-C_7$ normal paraffins-containing stream. The mixture is passed over two separators, normal $C_5-C_7$ paraffins being adsorbed on special zeolite beds and isoparaffins plus normal $C_4$ paraffins passing through these beds.

At the same time normal paraffins are desorbed from one or more zeolite beds contained in a third separator by passing a hydrogen-containing gas over the zeolite beds. Intermittently, the separators are used for adsorption and desorption. In this way, normal $C_5-C_7$ paraffins are desorbed from the content of separator 501 by passing the hydrogen-containing gas supplied via line 14 over the zeolite beds in the separator. The normal $C_5-C_7$ paraffins and hydrogen-containing mixture is withdrawn from the separator 501 and recycled via lines 3 and 4 to the isomerization/hydrocracking reactor 10.

$C_4-C_7$ isoparaffins and normal $C_4$ paraffins not being adsorbed by the zeolite beds in separators 502 and 503 pass through these separators and are withdrawn as a product from the system via line 16, line 17 and line 18.

This $C_4-C_7$ isoparaffins and $C_4$ normal paraffins mixture is preferably separated into normal butane and iso-butane and a $C_5-C_7$ isoparaffins mixture. The latter is an excellent motor gasoline blending component having a high octane number and a desired volatility. The iso-butane can be used for the production of $C_7$ and $C_8$ isoparaffins by alkylation, and of methyl tertiary butyl ether and tertiary butyl alcohol. These products are also excellent motor gasoline blending components. N-butane can also be blended into the gasoline up to the limits set by vapor pressure specifications.

In FIG. 2, a process is schematically shown for the production of a $C_4-C_7$ isoparaffins-containing gasoline blending component, a $C_3$ and $C_4$ olefins-containing chemical feedstock, a kerosine fraction and a gas oil fraction.

To this end the effluent from a Fischer-Tropsch hydrocarbon synthesis step, i.e., a heavy paraffins-containing hydrocarbon mixture, is introduced into the process via line 1 and passed to a high temperature separator 19 operating at a temperature in the range from about 200° C. to about 350° C. and a pressure in the range from about 20 bar to about 40 bar. In this separator 19, the Fischer-Tropsch effluent is separated into a gaseous stream containing hydrogen and light (e.g. $C_{10}-$) hydrocarbons and a heavy liquid fraction boiling above about 150° C. and containing $C_{10}+$ hydrocarbons. The gaseous stream is cooled and partially condensed in a cooler (not shown) and passed through line 21 to a low temperature separator 22 wherein it is separated into gas containing hydrogen and mainly $C_1-C_4$ hydrocarbons, a liquid aqueous stream which is withdrawn from the system via line 24 and a liquid hydrocarbon stream comprising mainly $C_4+$ paraffins. The gas is highly olefinic and therefore a desired feedstock for the chemical industry or for the production of highly branched isoparaffins by alkylation. It is withdrawn from the system via line 23.

The liquid hydrocarbon stream comprising paraffins is passed through line 25 and line 4 to an isomerization/hydrocracking reactor 10.

The heavy liquid stream obtained from the separator 19 and comprising $C_{10}+$ hydrocarbons is combined via line 26 with a bottoms recycle stream passed via line 2 from the fractionator 30 and containing $C_{20}+$ paraffins.

The combined streams are further combined via line 27 with a hydrogen-containing gaseous stream transferred via line 6, a recycle gas compressor 40, line 14 and line 28. The combined liquid and gaseous streams are passed via line 29 to a heavy paraffins hydrocracking reactor 60. In this reactor heavy paraffins are hydrocracked at a temperature in the range from about 250° C. to about 400° C. and pressure in the range from about 20 bar to about 50 bar. Preferably, a catalyst which contains from about 0.1% by weight to about 2% by weight, even more preferably from about 0.2% by weight to about 1% by weight, of one or more noble metals of Group VIII supported on a carrier is used. Preference is given to catalysts containing platinum or palladium as the noble metal. Examples of suitable carriers for the noble metal catalysts include but are not limited to, amorphous oxides of the elements of Groups II, III and IV, such as silica, alumina, magnesia and zirconia and also mixtures of these oxides, such as silica-alumina, silica-magnesia and silica-zirconia. The preferred carrier for the noble metal catalysts is silica-aluminas.

The effluent from the hydrocracking reactor 60 is passed through line 31 to a product separator 20 where it is combined with the effluent from the isomerization/hydrocracking reactor 10. This effluent has been formed by isomerizing and hydrocracking the liquid hydrocarbon stream from line 4 using hydrogen-containing gas which has been obtained via line 3 from an iso/normal paraffin separator 501. In the separator 20 the combined streams are separated into a hydrogen-rich gaseous stream and a higher boiling hydrocarbons-containing liquid stream.

The gaseous stream is recycled in part through lines 6, 14, 28 and 29, by the recycle gas compressor 40 to the hydrocracking reactor 60 while a bleed stream from this gaseous stream is withdrawn from the system via line 12. The liquid stream is passed through line 7 to the fractionator 30 where it is separated into a gas containing traces of hydrogen and $C_1$-$C_3$ hydrocarbons, a liquid $C_4$-$C_7$ containing light naphtha stream, a kerosine stream (boiling in the range from about 150° C. to about 250° C.) and a gas oil stream (boiling in the range from about 250° C. to about 370° C.).

The gas is withdrawn from the system via line 8 and line 12. The kerosine and gas oil are withdrawn as products from the system via line 32 and line 33 respectively. These products consist mainly of paraffins that are of excellent quality.

The light naphtha stream is passed via line 9, line 91 and line 92 to the iso/normal paraffins separators 502 and 503 where an isoparaffins ($C_4$-$C_7$) and normal butane-containing stream, an excellent gasoline blending component, is separated. It is withdrawn from the system via lines 16, 17 and 18, while normal $C_5$-$C_7$ paraffins are being adsorbed on the zeolite beds contained in the separators 502 and 503.

A desorption cycle follows in which the normal paraffins are desorbed from the zeolite beds as is the case with the normal paraffins having been adsorbed in separator 501 in a former adsorption cycle (not shown). In the scheme shown in FIG. 2 hydrogen-containing gas is passed through the lines 14 and 15 and adsorber 501 thereby desorbing normal paraffins from the zeolite bed(s) contained in the adsorber 501 which normal paraffins are recycled through lines 3 and 4 to the isomerization/hydrocracking reactor 10.

FIG. 3 is a schematic representation of a process for the production of high octane $C_4$-$C_7$ isoparaffin gasoline components, high cetane gas oil and low smoke point kerosine from a heavy paraffinic synthetic hydrocarbon product. The latter is introduced into the process via line 1 and combined with a heavy paraffins ($C_{20}+$)-containing recycle stream transferred from a fractionator 31 through line 26. The combined streams are passed through line 27 and combined with a hydrogen and light (mainly $C_1$-$C_3$) hydrocarbon-containing gas supplied via line 28. The combined streams are passed via line 29 to a heavy paraffins hydrocracking reactor 60.

In this reactor the heavy paraffins are hydrocracked using a similar catalyst and reaction conditions as described hereinbefore with reference to the reactor 60 of FIG. 2.

The effluent from the reactor 60 is passed via line 21 to a product separator 24 where it is separated into a hydrogen and light hydrocarbons (mainly $C_1$-$C_3$)-containing gas and a higher boiling hydrocarbons-containing liquid stream containing hydrocarbons from $C_4$ upward. The gas is in part recycled through line 61, a recycle gas compressor 24 and lines 28 and 29 to the reactor 60, make-up hydrogen being supplied via line 25. The remaining part of the gas is withdrawn from the system as a bleed stream via line 22.

The liquid stream is passed via line 11 to the fractionator 31 by means of which it is separated into a paraffinic naphtha ($C_4$ to $C_{10}$), a kerosine (boiling in the range from about 150° C. to about 250° C. and having a smoke point of at least about 40 millimeters), a gas oil (boiling in the range from about 250° C. to about 370° C. and having a cetane number of at least about 60 and a heavy paraffins-containing bottom product (boiling above about 370° C. The kerosine and the gas oil are withdrawn from the process as final products via line 32 and line 33 respectively. The bottom product is recycled to the reactor 60 via lines 26, 27 and 29.

The paraffinic naphtha is passed via line 34 to line 4 wherein it is combined with a hydrogen and normal paraffins-containing recycle stream supplied via line 2. The combined streams 34 and 2 are introduced via line 4 into the isomerization/hydrocracking reactor 10 wherein higher boiling normal paraffins are at least in part catalytically hydrocracked and lower boiling normal paraffins are at least in part catalytically isomerized in the presence of hydrogen.

The effluent from reactor 10 is passed via line 5 to product separator 20 where it is separated into a hydrogen and light hydrocarbons (mainly $C_1$-$C_3$)-containing gaseous stream and a higher boiling hydrocarbons ($C_4$-$C_{10}$)-containing liquid stream. The gaseous stream is withdrawn via line 6. It is partly removed from the system via line 12 and partly recycled to an iso/normal paraffins separator via line 13, the recycle gas compressor 40 and line 14.

The liquid stream is passed through line 7 to the fractionator 30 where it is separated into a light hydrocarbons (mainly $C_3$)-containing gas stream, a $C_4$-$C_7$ iso/normal paraffins-containing liquid stream and a $C_8+$ hydrocarbons-containing liquid stream. The gas stream is withdrawn from the system via line 8 and line 12. The C$_8$+ hydrocarbons-containing liquid stream is recycled via line 2, wherein it is combined with a normal C$_5$–C$_7$ paraffins-containing stream from line 3, and the line 4 to the isomerization/hydrocracking reactor 10. The C$_4$–C$_7$ iso/normal paraffins-containing liquid stream is passed via lines 9, 91 and 92 to iso/normal paraffins separators 502 and 503.

In these separators, normal C$_5$–C$_7$ paraffins are adsorbed on zeolite beds, while C$_4$–C$_7$ isoparaffins and C$_4$ normal paraffins pass through these beds and are withdrawn from the system as final products via lines 16, 17 and 18. At the same time, normal C$_5$–C$_7$ paraffins are desorbed from one or more zeolite beds contained in an iso/normal paraffins separator 501 to which they had been adsorbed during a former process cycle (not shown). The desorption is effected by passing the light hydrocarbons and hydrogen-containing stream in line 14 over the zeolite bed(s). Fresh make-up hydrogen is introduced to the system via line 15.

A gaseous mixture of hydrogen, light hydrocarbons and desorbed C$_5$–C$_7$ normal paraffins is recycled via lines 3, 2 and 4 to the isomerization/ hydrocracking reactor 10.

The process of the present invention is further described in the following examples which are provided for illustrative purposes only and are not to be construed as limiting the invention.

ILLUSTRATIVE EMBODIMENT

In the instant process as depicted in FIG. 1, 100 t/d of a hydrocarbon product from a Fischer-Tropsch synthesis plant (not shown) was introduced together with 80 t/d of a recycle stream mainly consisting of C$_8$+ paraffins and a gas comprising 15 t/d hydrogen and 25 t/d recycled normal C$_4$–C$_7$ paraffin. Each of these were introduced into the isomerization/hydrocracking reactor.

The Fischer-Tropsch product had been obtained from synthesis gas having a H$_2$:CO ratio of 2:1 using a catalyst consisting of 30 pbw Co, 12 pbw Zr deposited on 100 pbw SiO$_2$ by impregnation. The conditions during the hydrocarbon synthesis were:

| | |
|---|---|
| Temperature: | 220° C. |
| Pressure: | 30 bar |
| Space velocity: | 600 nm$^3$/nm$^3$/hr. |

The Fischer-Tropsch product consisted mainly of paraffins boiling in the range from 20° C. to 500° C. and for 80% by weight of heavy paraffins boiling in the range from 150° C. to 500° C.

In the isomerization/hydrocracking reactor the Fischer-Tropsch effluent was converted to a lower boiling iso/normal paraffins-containing mixture. In the reactor a catalyst was used consisting of 0.4 pbw Pt deposited on 100 pbw zeolite Y being in the hydrogen form and having a Na content of 0.05% by weight. The reaction conditions were:

| | |
|---|---|
| Temperature: | 300° C. |
| Pressure: | 20 bar |
| Partial hydrogen pressure: | 15 bar |
| Space velocity: | 1 kg/kg/hr. |

The isomerization/hydrocracking product was separated in separator 20 in a hydrogen-rich gas and 203 t/d condensate and the latter further separated in fractionator into 13 t/d of a light hydrocarbons-containing bleed stream, 110 t/d of a C$_4$–C$_7$ iso/normal paraffins-containing stream and 80 t/d of a heavy paraffins-containing recycle stream.

To the hydrogen and light hydrocarbons-containing gas 2.5 t/d fresh hydrogen make-up gas was added via line and the resulting gas mixture was passed over a zeolite bed contained in adsorber 501 to desorb 25 t/d normal C$_5$–C$_7$ paraffins which were recycled to the reactor.

From the C$_4$–C$_7$ iso/normal paraffins-containing stream 9 85 t/d of a C$_4$–C$_7$ isoparaffins- and C$_4$ normal paraffins-containing mixture was separated by passing stream 9 over 2 zeolite beds, comprising zeolite 5A as an absorbent and contained in absorbers. The isoparaffins and nC$_4$ paraffins mixture was removed from the system as a final product. This mixture consisted of:

| | |
|---|---|
| nC$_4$ + iC$_4$: | 23% by weight |
| iC$_5$: | 40% by weight |
| iC$_6$: | 29% by weight |
| iC$_7$: | 8% by weight. |

It was separated into an i-butane product, a n-butane product and a C$_5$–C$_7$ isoparaffins mixture. The iC$_4$ paraffins were used as a feedstock for an alkylation process.

The C$_5$–C$_7$ isoparaffins were used as a motor gasoline blending component having a RON (octane number determined by the research method) of 86 and a MON (octane number determined by the motor method) of 85.

What is claimed is:

1. A process for the production of isoparaffins having 4 to 7 carbon atoms per molecule from synthesis gas comprising the following steps:
    a) synthesizing a heavy paraffins-containing hydrocarbon mixture over a Fischer-Tropsch catalyst;
    b) converting at least part of the heavy paraffins-containing hydrocarbon mixture over a bi-functional isomerization/hydrocracking catalyst comprising at least one catalytically active metal chosen from the metals of Groups VIB, VIIB, VIII and mixtures thereof and a zeolite having a pore diameter from about 0.5 nanometers to about 1.0 nanometers and a silica:alumina ratio from about 5 to about 200 under isomerization/hydrocracking conditions;
    c) separating normal paraffins from at least part of the isoparaffins-containing product of step (b); and
    d) recycling at least part of the normal paraffins to step (b) and withdrawing C$_4$–C$_7$ isoparaffins as a product from the process.

2. The process of claim 1 wherein the Fischer-Tropsch catalyst satisfies the relation:

$$(3+4R) > L/S > (0.3+0.4R)$$

wherein
L = the total quantity of cobalt present on the catalyst, expressed as mg Co/ml catalyst,
S = the surface area of the catalyst, expressed as m$^2$/ml catalyst, and
R = the weight ratio of the quantity of cobalt deposited on the catalyst by kneading to the total quantity of cobalt present on the catalyst.

3. The process of claim 2 wherein the Fischer-Tropsch catalyst utilized in step (a) comprises a silica carrier, cobalt in an amount from about 3 pbw to about 60 pbw, and zirconium in an amount from about 0.1 pbw to about 100 pbw per 100 pbw of silica carrier.

4. The process of claim 2 wherein step (a) is carried out at a temperature of from about 125° C. to about 350° C. and a pressure of from about 5 bar to about 100 bar.

5. The process of claim 1 wherein the zeolite has an alkali metal content of less than about 0.1% by weight.

6. The process of claim 1 wherein the catalyst contains from about 0.05 pbw to about 5 pbw of a metal selected from the group consisting of platinum, palladium, or mixtures thereof per 100 pbw of zeolite.

7. The process of claim 1 wherein the catalyst contains from about 0.1 pbw to about 35 pbw of at least one non-noble metal selected from the group consisting of Groups VIB, VIIB, VIII of the Periodic Table of Elements and mixtures thereof, per 100 pbw of zeolite.

8. The process of claim 1 wherein step (b) is carried out at a temperature of from about 250° C. to about 350° C., a pressure of from about 7 bar to about 15 bar, an hourly space velocity of from about 0.2 kg to about 20 kg of hydrocarbon feed per kg of catalyst per hour and a hydrogen/hydrocarbon feed molar ratio of from about 1 to about 50.

9. The process of claim 1 wherein at least part of the product of step (b) is separated by fractional distillation to obtain a $C_7-$ fraction and a $C_8+$ fraction, at least part of the $C_8+$ fraction is recycled to step (b) and at least part of the $C_7-$ fraction is passed to step (c).

10. The process of claim 1 wherein step (c) is carried out by contacting at least part of the effluent of step (b) with a separatory molecular sieve capable of adsorbing normal hydrocarbons, whereby a product stream containing branched hydrocarbons is separated off.

11. The process of claim 10 wherein in step (c) the adsorbed normal hydrocarbons are desorbed from the molecular sieve by passing a hydrogen-containing gas over the molecular sieve and passing at least part of the hydrogen-containing effluent of step (c) to step (b).

12. The process of claim 10 wherein the separatory molecular sieve has a pore diameter in the range from about 0.3 nanometers to about 0.8 nanometers.

13. The process of claim 12 wherein the separatory molecular sieve has a pore diameter in the range from about 0.4 nanometers to about 0.6 nanometers.

14. The process of claim 10 wherein the adsorption in step (c) is carried out at a temperature in the range from about 100° C. to about 300° C. and a pressure in the range from about 5 bar to about 25 bar.

15. The process of claim 11 wherein the desorption in step (c) is carried out at a temperature in the range from about 200° C. to about 450° C. and a pressure in the range from about 1 bar to about 25 bar.

16. The process claim 1 wherein at least part of the heavy paraffins-containing hydrocarbon mixture is hydrocracked in a hydrocracking reactor, the effluent of the hydrocracking reactor is separated into a hydrogen-containing gas which is at least in part recycled to the hydrocracking reactor, a naphtha fraction which is at least in part passed to the step (b), a kerosine fraction and a gas oil fraction which are withdrawn as products from the process, and a heavy fraction which is at least in part recycled to the hydrocracking step.

17. The process of claim 16 wherein the heavy paraffins-containing hydrocarbon mixture is separated into a heavy fraction boiling above about 150° C. and a light fraction containing $C_{10}-$ hydrocarbons, the heavy fraction is passed to the hydrocracking step and the light fraction is passed to the step (b).

18. The process of claim 17 wherein the effluents of the hydrocracking step and of the step (b) are combined and the combined effluents are separated into a hydrogen-containing gas which is at least in part recycled to the hydrocracking step and/or to the step (b), a naphtha fraction which is at least in part passed to the step (b), a kerosine fraction and a gas oil fraction which are withdrawn as products from the process, and a heavy fraction which is at least in part recycled to the hydrocracking step.

* * * * *